United States Patent
Lin

(10) Patent No.: US 11,517,683 B2
(45) Date of Patent: Dec. 6, 2022

(54) SYRINGE FOR DETECTING PRESSURE CHANGE

(71) Applicant: FLATMED, LLC., Taipei (TW)

(72) Inventor: Li-Yu Lin, Taipei (TW)

( * ) Notice: Subject to any disclaimer, the term of this patent is extended or adjusted under 35 U.S.C. 154(b) by 495 days.

(21) Appl. No.: 16/490,076

(22) PCT Filed: Mar. 9, 2018

(86) PCT No.: PCT/US2018/021636
§ 371 (c)(1),
(2) Date: Aug. 30, 2019

(87) PCT Pub. No.: WO2018/208367
PCT Pub. Date: Nov. 15, 2018

(65) Prior Publication Data
US 2020/0069889 A1    Mar. 5, 2020

Related U.S. Application Data

(60) Provisional application No. 62/503,954, filed on May 10, 2017.

(51) Int. Cl.
*A61M 5/48* (2006.01)
*A61M 5/315* (2006.01)

(52) U.S. Cl.
CPC ........ *A61M 5/486* (2013.01); *A61M 5/31515* (2013.01); *A61M 2205/6081* (2013.01)

(58) Field of Classification Search
CPC .... A61M 5/486; A61M 5/31515; A61M 5/48; A61M 5/315; A61M 2205/6081; A61B 5/7445; A61B 5/03; A61B 17/3401
See application file for complete search history.

(56) References Cited

U.S. PATENT DOCUMENTS

| | | | | |
|---|---|---|---|---|
| 4,064,879 A | * | 12/1977 | Leibinsohn | A61M 5/486 604/218 |
| 4,759,750 A | * | 7/1988 | DeVries | A61M 5/315 116/DIG. 17 |

(Continued)

FOREIGN PATENT DOCUMENTS

| CN | 104703649 | 6/2015 |
|---|---|---|
| JP | S 52-151287 A | 12/1977 |

(Continued)

OTHER PUBLICATIONS

Office action by JPO, dated Nov. 2, 2021.

*Primary Examiner* — Tasnim Mehjabin Ahmed
(74) *Attorney, Agent, or Firm* — OPES IP Consulting Co., Ltd.

(57) ABSTRACT

A device for positioning a needle tip to a desired location by signaling pressure change is provided. The device includes a barrel, a piston, a biasing element, and a plunger. The barrel defines a reservoir, and it includes a distal end connectable to a puncturing apparatus. The plunger is slidably engaged with the piston, and both are movable within the reservoir. The biasing element connects the plunger and the piston, and its change in length corresponds to the relative position of the plunger and piston. In operation, the piston is at a first position relative to the plunger when the biasing element is at a first length. The piston later moves to a second relative position in response to the biasing element's change of the length resulting from a pressure change inside the reservoir when the puncturing apparatus reaches a location of a mass. The position's change of the piston is visually detectable.

23 Claims, 11 Drawing Sheets

(56) References Cited

U.S. PATENT DOCUMENTS

| | | | |
|---|---|---|---|
| 4,838,864 A | | 6/1989 | Peterson |
| 5,722,955 A | * | 3/1998 | Racz ................. A61M 5/31511 |
| | | | 604/121 |
| 2007/0244446 A1 | * | 10/2007 | Sundar ............... A61B 17/3401 |
| | | | 604/218 |
| 2017/0014573 A1 | | 1/2017 | Ogawa |

FOREIGN PATENT DOCUMENTS

| | | | |
|---|---|---|---|
| JP | 2006-516436 A | 7/2006 | |
| JP | 4505561 | 7/2010 | |
| JP | 2012-525947 A | 10/2012 | |
| WO | WO2007/032352 | 3/2007 | |
| WO | WO-2020219404 A1 * | 10/2020 | ........ A61M 5/31505 |

* cited by examiner

10

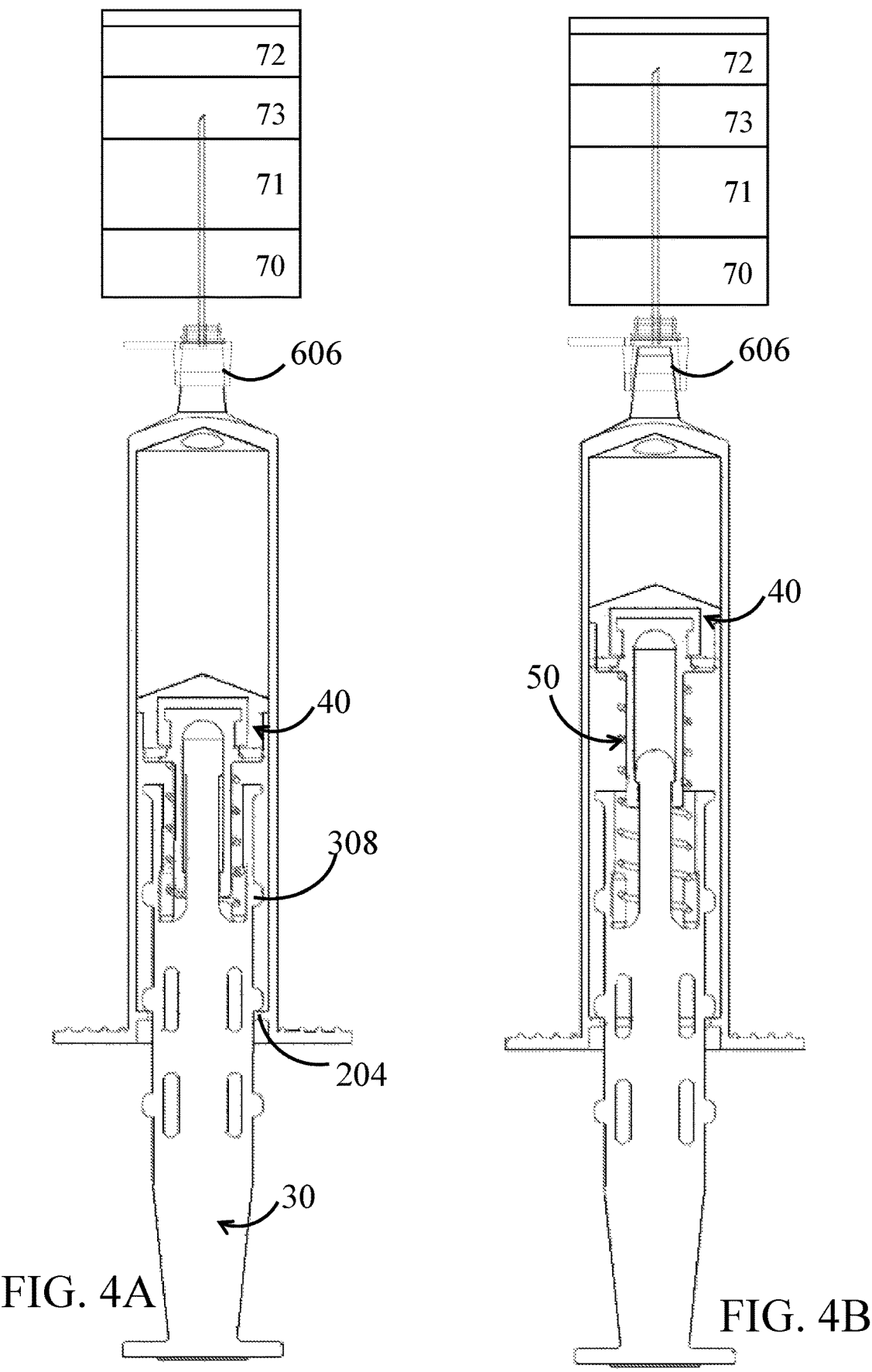

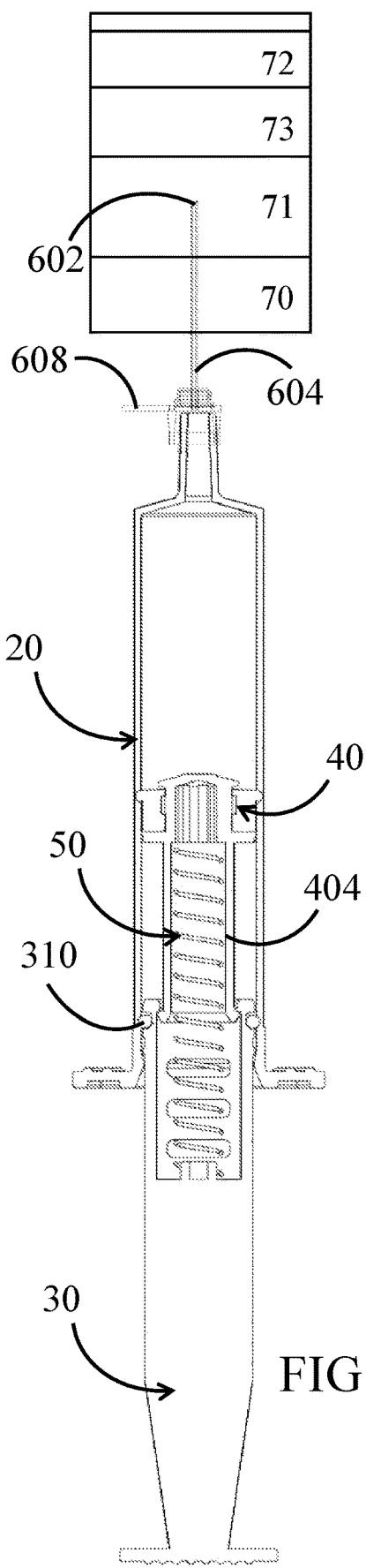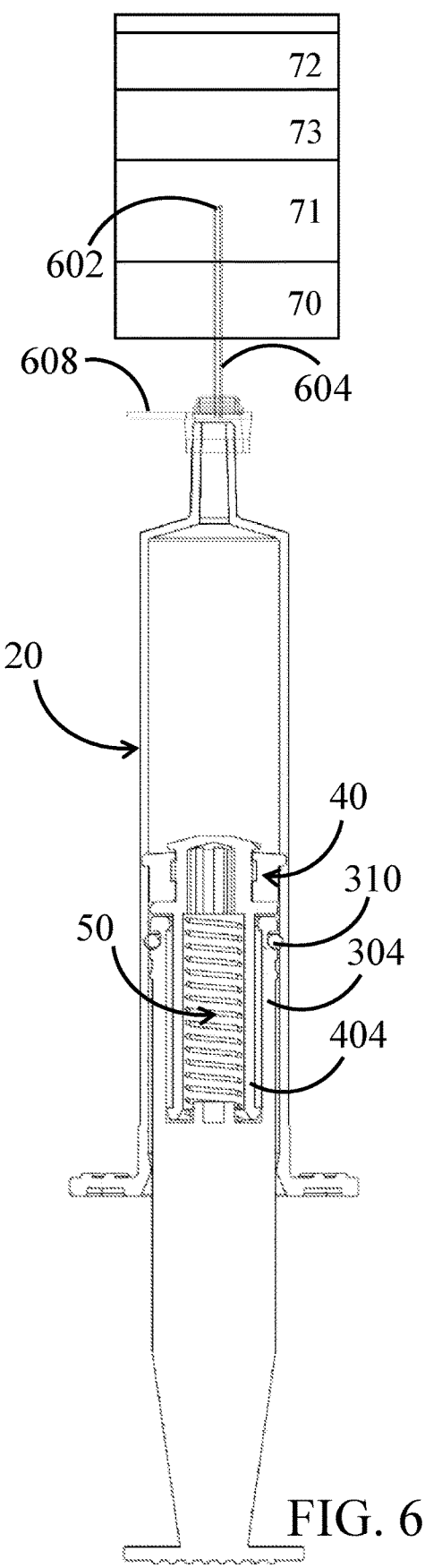
FIG. 6A
FIG. 6B

SYRINGE FOR DETECTING PRESSURE CHANGE

CROSS REFERENCE TO RELATED APPLICATION

The present application claims priority to U.S. Provisional Application Ser. No. 62/503,954 filed on May 10, 2017, which is incorporated by reference in their entirety.

FIELD

The present disclosure relates to a syringe and more particularly to a syringe for identifying a body cavity.

BACKGROUND

Medical devices, such as needles and catheters, may be inserted into a patient's body for various purposes. However, the insertion of a needle is a risky procedure. If the needle head reaches an improper location within a human body, there may be serious complication. Different kinds of techniques have been employed to detect the location of a needle tip. One of most common practices for identifying the location of a needle tip is by detecting pressure change. Specifically, different body cavities or parts (e.g., a vein or an artery) feedback different levels of pressure to the needle tip. For example, a pressure drop may mean that the needle head has moved from one body part with a higher pressure to another body part with a lower pressure. Such technique is commonly used in epidural injection and in the insertion of the central venous catheter (hereinafter "CVC"). Epidural nerve block performed by the epidural injection is a regional anesthesia technique. It has been proven highly useful in the following procedures: obstetrical analgesia, surgical anesthesia, postoperative analgesia, and chronic pain control. Local anesthetics or steroids are injected into the epidural space. The medicine injected diffuses through the dura, and further blocks the signal transmission of nerve fibers in the spinal cord. The result is a reversible loss of sensation and awareness.

Epidural is a sub-atmospheric space between the ligamentum flavum and the dura mater. To inject medication into the epidural, both midline and paramedian approaches require placing a needle tip into the epidural. For the midline approach, the needle pierces through the skin, subcutaneous tissue, interspinous ligament and ligamentum flavum to reach the epidural.

The traditional method for locating the needle tip is the "loss of resistance" technique (hereinafter "LOR") based on detection of pressure drop when the needle tip reaches the epidural. LOR is premised upon the epidural having lower pressure than other parts of the body along the puncturing route of the needle. Thus, a free injection of air or liquid from the syringe can be induced due to the result of the sudden loss of resistance of the syringe plunger. For instance, an anesthesiologist can detect the pressure drop by feeling the resistance change of the plunger coupled with the needle.

There are, however, some safety concerns associated with the LOR technique. The epidural is a very narrow space near the spinal cord. The advance of the needle must be stopped right after the needle tip reaches the epidural space to prevent accidental dural puncture. Otherwise, the result may be cerebrospinal fluid leakage followed by an intractable headache and injury to the spinal nerves. Today, the rate of accidental dural punctures is 2-5%. For less skilled and experienced operators, the failure rate is even higher because the traditional LOR technique depends heavily on the operator's ability to sense a delicate pressure change/resistance lost when the needle head reaches the epidural.

Some studies indicate that there is no significant difference between using air or saline in the LOR technique for the analgesia effect. However, it has been reported that a post dural puncture headache (hereinafter the "PDPH") is more easily induced if air, rather than saline, is used. The reasons may be that liquid is uncompressible, and that epidural may be simultaneously expanded when the needle pierces into the epidural. Accordingly, liquid may reduce the risk of dural puncture. Moreover, many cases report that errors in using the air-based LOR technique to locate needle tip lead to air injection into the spinal cord and induce severe complications, such as paraplegia and pneumocephalus.

U.S. Pat. No. 7,175,608 (Maan Hasan et al., 2003) disclosed a device capable of transforming the LOR hand feeling to a visual signal for detecting needle position. The device includes a diaphragm on one side, a one-way valve, multiple connections to the epidural needle, and a syringe. After the needle connects to the device and gas is provided, the diaphragm bulges outwardly due to the needle tip being blocked by the body mass. Subsequently, the diaphragm flattens while the needle tip arrives at a space/region with less pressure (e.g., the epidural). A visual endpoint is provided to assist the procedure. However, such device is known for vulnerability during surgical procedures and is only suitable for the air-based LOR procedure, which covers only a fraction of epidural injections nowadays.

U.S. Pat. No. 8,197,443 (Sundar Satish et al., 2007) disclosed another detection device for locating the needle in epidural. The major principle here is to achieve a balance between the pressure in the barrel and the spring force in the device, whereas the pressure in the barrel is equal to the pressure at the needle tip. First, an operator needs to pull the plunger to draw saline into the device and compresses the spring. Next, the operator keeps the plunger in a certain position relative to the syringe to prevent the saline from exiting the syringe and attaches the syringe to a hub of the needle. The syringe supplies a constant pressure in the above procedure, and the liquid will remain in the syringe. When the pressure in the needle tip becomes less than the spring force, the spring releases, and the piston and plunger both move forward. Although the syringe provides a visual signal to facilitate the localization procedure, it contains several defects in actual practices. For example, the compressed spring provides a force to the fluid (e.g., saline) in the syringe, and it may accidentally release the fluid if the syringe and the needle are not secured properly. In addition, because there is no fixing element on the plunger to affix the plunger, the device needs to be completely removed before withdrawing the needle or adjusting the needle direction to prevent accidental fluid injection into subcutaneous tissue.

U.S. Pat. No. 9,186,172 (Velez Rivera et al., 2009) disclosed another device that aims to overcome the aforementioned drawbacks. It provides a securing mechanism capable of securing the plunger. When the securing means is released, the plunger can freely move from a starting position to a final position once the needle tip reaches the epidural. However, the releasing of the securing means is not readily reversible during surgical operation. The needle may be blocked by subcutaneous tissue accumulated during insertion if the operator forces the device to change from a released to a fixed state. The foregoing reduces the device flexibility in procedures. Moreover, adding a securing mechanism means additional component and more complicated structure.

The insertion of a central venous catheter is another technique based on detection of pressure change. CVC may be applied for many purposes, such as monitoring a fluid resuscitation, drug administration, dialysis and diagnostic studies. In preparation of the insertion of the CVCs, the operator will insert a small-bore needle (e.g., 23G needle) into a vein of the body mass. After correct position is confirmed, a device with a larger diameter is inserted to create an insertion hole large enough for CVC. The key step of the entire procedure is to determine whether the needle tip is placed in the vein rather than the artery or other regions. One of the examination technique is through pressure detection. If the needle tip is not placed properly, the entire CVC procedure will be compromised and the result may be serious wounds (e.g., stroke or death) to the patient. However, according to statistical results, about 3-25% of the patients experience complications during or post CVC procedure. For example, about 2-4.5% of the patients have accidental arterial puncture. A technique to reduce the risks during CVC procedure is needed.

In some cases, ultrasound guidance may be used to reduce the risk of CVCs. Nevertheless, it is rarely employed in the clinical setting. A survey reports that about 67% of the physicians almost never use ultrasound during CVC insertion.

In some other case, a manometer may be used to measure the central venous pressure. However, the application of a typical manometer is inconvenient. The external transducer must be placed at a height approximately level to patient's right atrium. Incorrect transducer position may result in an erroneous measurement. Furthermore, the saline solution used to measure the pressure is in direct contact with the biological fluid in the blood vessel, further increase the risk of infection. U.S. Pat. No. 8,926,525 disclosed another device for solving the problems related to traditional manometers. Such device includes a sensing unit, a processing unit, and an output unit covered by a housing. The output unit transmits a reporting signal based on a determined pressure. When such device is connected to the needle, the operator will know the pressure in the needle tip and thereby reduce the risk of incorrect central venous catheterization. However, such sensing device is costly and therefore still infrequently used in clinical procedures.

Based on the foregoing, a novel device capable of overcoming the aforementioned drawbacks is required.

SUMMARY

The present disclosure teaches a syringe for detecting pressure change while also providing visually detectable signal to the operator of the syringe. The syringe includes a barrel, a piston, a biasing element, a plunger, and a puncturing apparatus. The barrel defines a reservoir for receiving a constituent and includes a proximal end and a distal end with an outlet. The plunger is slidably engaged with the piston, and both are movable within the reservoir. The biasing element is disposed between the plunger and the piston, and the relative position of the plunger and piston corresponds to the biasing element's change in length. The puncturing apparatus is detachably connected to the distal end of the barrel, thus the internal volume of the barrel is communicative with the outside environment via the puncturing apparatus. The piston is at a first position relative to the plunger when the biasing element is at a first length. The piston further moves from the first position to a second position in response to the biasing element's change of the length resulting from a pressure change inside the reservoir caused by the puncturing apparatus reaching a location of a mass. Furthermore, the position's change of the piston is visually detectable.

In some embodiments, the plunger includes a stopper for creating a resistance between the barrel so as to secure the plunger at a position relative to the barrel before or during operation of the syringe.

In some embodiments, the stopper is a ring made of elastomer.

In some embodiments, the constituent is in liquid or gas form.

In some embodiments, the biasing element includes a spring.

In some embodiments, the plunger receives the biasing element.

In some embodiments, the puncturing apparatus includes a needle tip.

In some embodiments, the piston moves from the first position to the second position relative to the plunger when the pressure inside the reservoir is decreasing.

In some embodiments, the piston moves from the first position to the second position relative to the plunger when the pressure inside the reservoir is increasing.

In some embodiments, the increasing pressure may be to more than zero or more than 2 kPa.

In some embodiments, the material of the biasing element includes metal, plastic, rubber or any combination thereof.

In some embodiments, the location of the mass is filled with a pressurized constituent including liquid, gas or a combination thereof.

In some embodiments, the location of the mass is a cavity.

In some embodiments, the direction of the piston from the first position to the second position is moving towards the plunger.

In some embodiments, the direction of the piston from the first position to the second position is moving away from the plunger.

In some embodiments, the piston is at least partially received by the plunger.

In some embodiments, the degree of compression of the biasing element is less when the piston is in the second position than in the first position.

In some embodiments, the degree of compression of the biasing element is more when the piston is in the second position than in the first position.

In some embodiments, the piston is at the first relative position when the puncturing apparatus enters the mass but before reaching the desired location.

Therefore, the device of the present disclosure translates pressure change into human identifiable signal. It provides a visual signal more readily and easily identifiable by an operator. The information of pressure change can be easily obtained by observing the elongated position change between the piston and the plunger. The simple design of the present device serves to reduce the risk of erroneous/pseudo read by the operator and to provide a less costly option for relevant operations.

In certain embodiments, the device of the present disclosure is equipped with a switch mechanism allowing for the change between observation modes (e.g., a sensing and a non-sensing mode). Such different modes may facilitate the adjustment/replacement of needles or other instruments during the procedures and may help to reduce the risk of erroneous/pseudo read.

BRIEF DESCRIPTION OF THE DRAWINGS

One or more embodiments are illustrated by way of example, and not by limitation, in the figures of the accompanying drawings, wherein elements are having the same reference numeral designations represent like elements throughout. The drawings are not to scale, unless otherwise disclosed.

FIG. 3 series include four sectional views (FIG. 3A-3D) in accordance with some embodiments of the present disclosure.

FIG. 4 series include two sectional views (FIGS. 4A and 4B) in accordance with some embodiments of the present disclosure. FIG. 4A disclosed that the syringe with the needle is under the compressed length S2 and in the false positive condition; and FIG. 4B is a perspective view of a syringe after sensing the pressure changed during the second sensing mode.

FIG. 6 series include three perspective views (FIG. 6A-6C) and one perspective view (FIG. 6D) in accordance with some embodiments of the present disclosure. FIG. 6A is the syringe further including the needle at a non-sensing mode; FIG. 6B is the syringe with the needle at the sensing mode.

FIG. 9 series include two sectional views in accordance with some embodiments of the present disclosure.

Figure 1A:
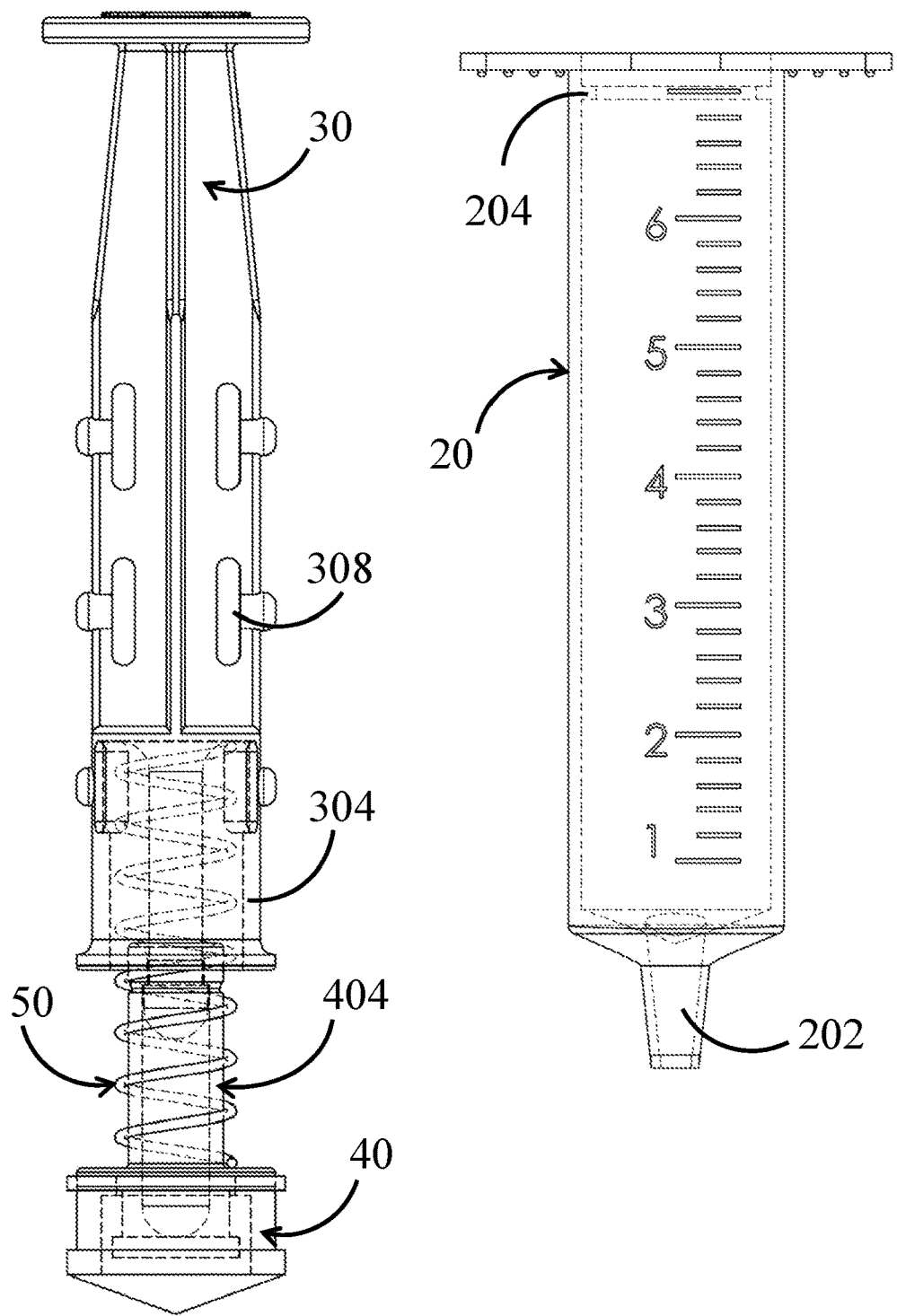
FIG. 1 series include a perspective view (FIG. 1A) and a sectional view (FIG. 1B) of a syringe in accordance with some embodiments of the present disclosure.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention. Any reference signs in the claims shall not be construed as limiting the scope. Like reference symbols in the various drawings indicate like elements.

DETAILED DESCRIPTION OF THE DISCLOSURE

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus in accordance with the present disclosure. It is to be understood that elements not specifically shown or described may take various forms. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

Definition

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise. Furthermore, relative terms, such as "bottom" and "top," may be used herein to describe one element's relationship to other elements as illustrated in the Figures.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

DETAILED DESCRIPTION

Figure 1B:
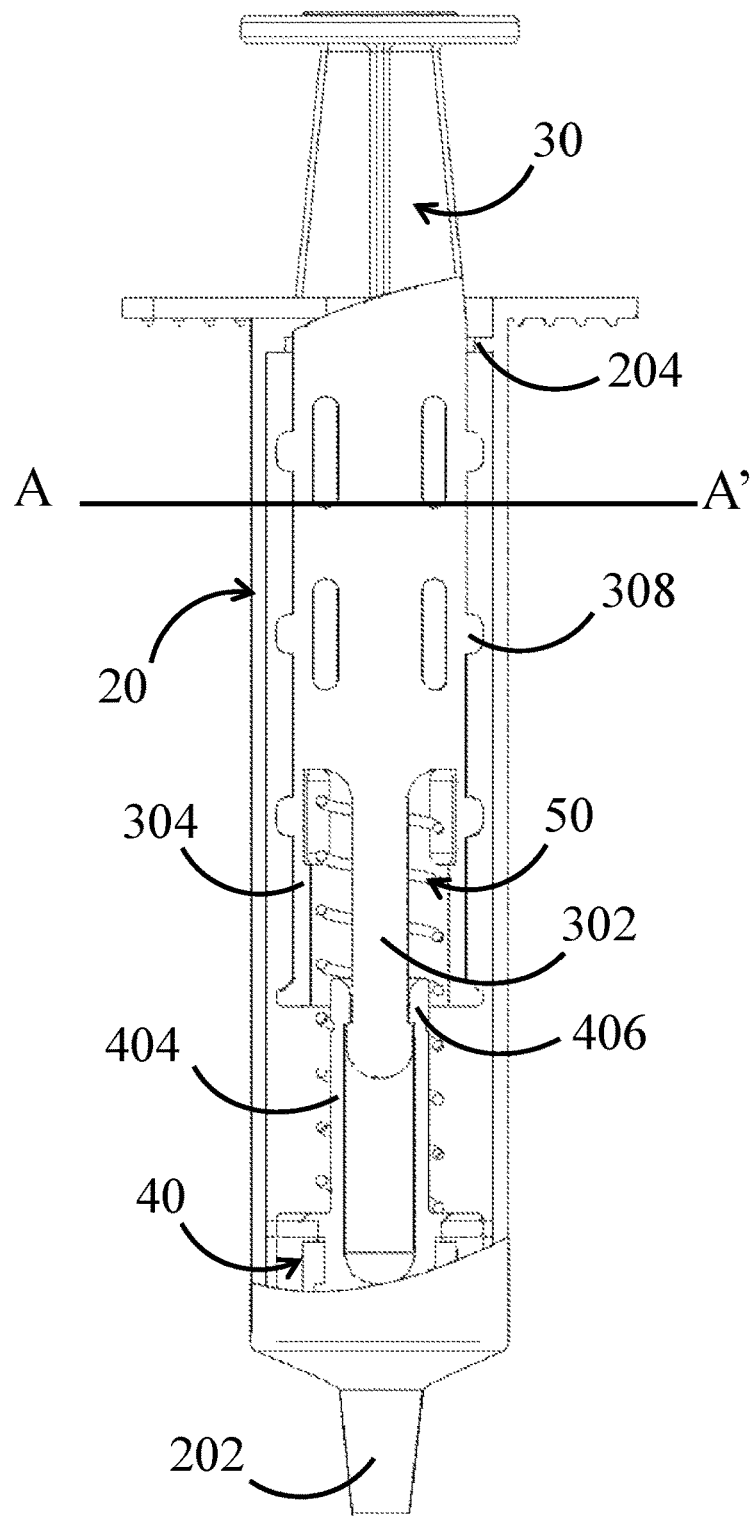

FIGS. 1A and 1B are schematic views of an exemplary embodiment of the disclosure. A device 10 for detecting pressure change in a body mass is provided. The device 10 may be in the form of a syringe or the like. The device 10 includes a barrel 20, a plunger 30, a piston 40 and a biasing element 50. The barrel 20 is a tubular cylinder with a connecting tube 202 at a distal end and an opening at an opposite proximate end. Through the opening, the barrel 20 receives and accommodates the plunger 30, the piston 40 and the biasing element 50. The barrel 20 may be coupled to and thus become fluid or gas communicative with other medical instruments, e.g., a tube or a needle, via the connecting tube 202. The barrel 20 includes, at its proximal end, a ring-shaped flange 204. The flange 204 decreases the diameter of the barrel 20 close to the opening, comparing to the regular diameter of its body, measured from the cross-section (e.g., line A-A'). The flange 204 serves to prevent the piston 40 or the plunger 30 from accidentally popping out of the barrel. The Flange 204 may be an integrated part of the barrel 20. Alternatively, it may be a separate component coupled to the barrel 20.

Once received, the plunger 30 and the piston 40 may move within the device 10 along a longitudinal axis (not shown) of the barrel 20. The plunger 30 and the piston 40 are connected by the biasing element 50. The biasing element 50 may be a spring or any apparatus capable of exerting counter-force when compressed or stretched. Moreover, the biasing element serves to adjust the relative position between the plunger 30 and the piston 40 during operation. An elongated bar may be optionally provided as an interface to increase the stability of the movement between the plunger 30 and the piston 40. Therefore, the piston 40 may optionally further includes a cylindrical body 404 with an outer wall defining an internal volume, which is communicative to the exterior via a throat 406 at the proximal end of the cylindrical body 404. The plunger 30 includes a mushroom shaped sliding part 302, a sheath 304 surrounding the sliding part 302 and a body having latches 308. The sliding part 302 is slideable within the cylindrical body 404. However, it is not readily removeable therefrom because the throat 406 acts as a stopper. The biasing element 50 (e.g., a spring) is configured to surround and connect the cylindrical body 404 of the piston 40 and the sliding part 302 of the plunger 30. FIG. 1B discloses the assembled device 10 before operation where the biasing element 50 of the device 10 has the maximal length in this state. Such state of the biasing element 50 is defined as a first length (i.e., a basic length S1). The biasing element 50 is compressed when the relative distance between the plunger 30 and the piston 40 decreases. In other words, the biasing element 50 is compressed when the sliding part 302 slides into the cylindrical body 404. In the foregoing state, the cylindrical body 404 is defined as being covered by the sheath 304. The barrel 20, the plunger 30, the piston 40 and the biasing element 50 constitute an exemplary syringe that is used to detect pressure change (i.e., the body cavity) with precision and translating such into an easily identifiable visual signal.

The device 10 of the present disclosure can be made by plastic, metal or any material suitable for medical instruments with zero or minimal toxicity to the subject (e.g., human). Furthermore, said material must also be able to withstand sterilization for medical purposes, such as high temperature, ethylene oxide (EtO) sterilization or any other methods known in the field. The primary materials used to manufacture the barrel 20 include polypropylene (the "PP"), polycarbonate (the "PC"), and high-density polyethylene (the "HDPE"). The primary materials used to manufacture the piston head include rubber, themoplasticomer (the "TPR"), themoplastic elastomer (the "TPE"), and ethylene propylene diene terpolymer (the "EPDM"). The primary material used to manufacture the piston body and the plunger 40 includes polypropylene (the "PP"), acrylonitrile butadiene styrene (the "ABS"), polycarbonate (the "PC"), polyethylene (the "PE"), and high-density polyethylene (the "HDPE"). The primary materials used to manufacture the biasing element 50 include metal, plastic, rubber or a combination thereof that is capable of providing a counter-force when compressed or deformed.

Figure 2:
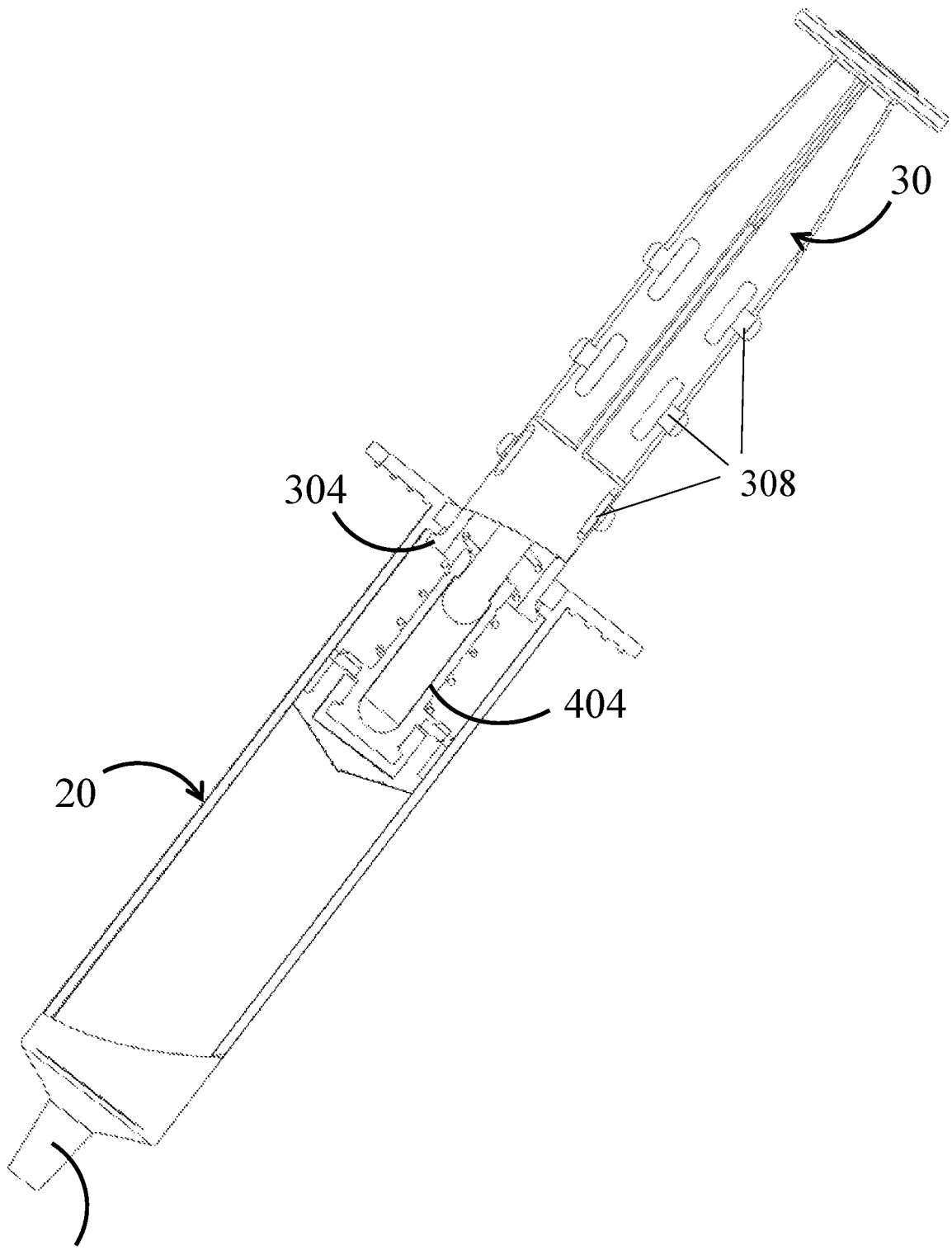
FIG. 2 is a sectional view of the fluid-contained syringe before using in accordance with some embodiments of the present disclosure.

The device 10 is capable of using gas or fluid/liquid as a constituent for detecting pressure change. In one embodiment, the syringe uses liquid (e.g., saline) as the constituent. FIG. 2 is a sectional view of the present disclosure that contains a constituent in the liquid form. As FIG. 2 shows, drawing the liquid into the barrel 20 can be achieved by pulling the plunger 30 outwardly. During such procedure, the syringe is in a non-sensing mode where the biasing element 50 is uncompressed or minimally compressed, and the sheath 304 of the plunger 30 does not cover the cylindrical body 404. In other words, the syringe cannot detect pressure change in the desire cavity (e.g., the body cavity) during the non-sensing mode.

Figure 3A:
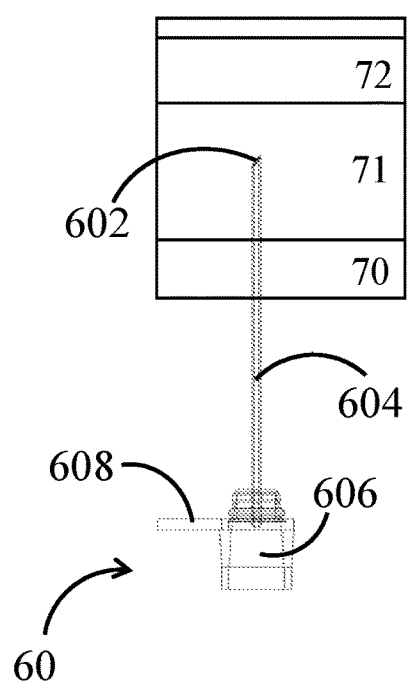
FIG. 3A is a needle located in a certain location of body.
Figure 3B:
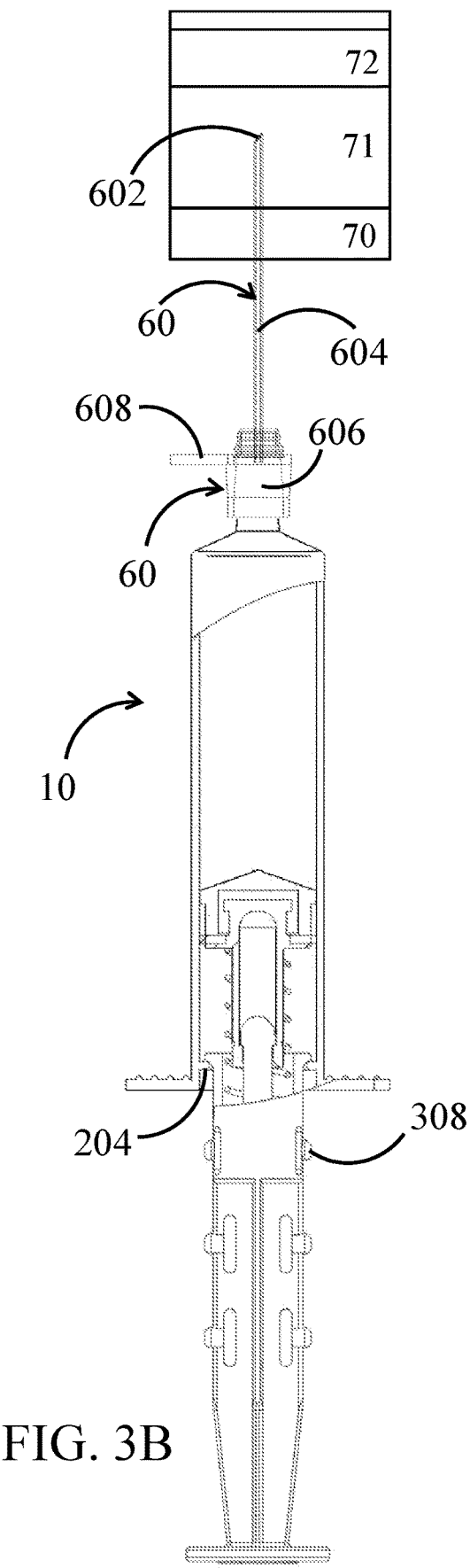
FIG. 3B is the needle further including a syringe.

FIG. 3A is the scenario where a needle 60 is inserted into a body mass (e.g., the skin 71 and subcutaneous tissue 72). The needle 60 includes a needle tip 602, a tubular needle 604, a hub 606 and a handle 608. Furthermore, as FIG. 3B shows, the needle 60 is connected to the device 10 by coupling the hub 606 of the needle 60 and the connecting tube 202 of the barrel 20 after the needle 60 pierces through the skin 71 and subcutaneous tissue 72 in sequence (about 3 cm depth).

Figures 3C, 3D:
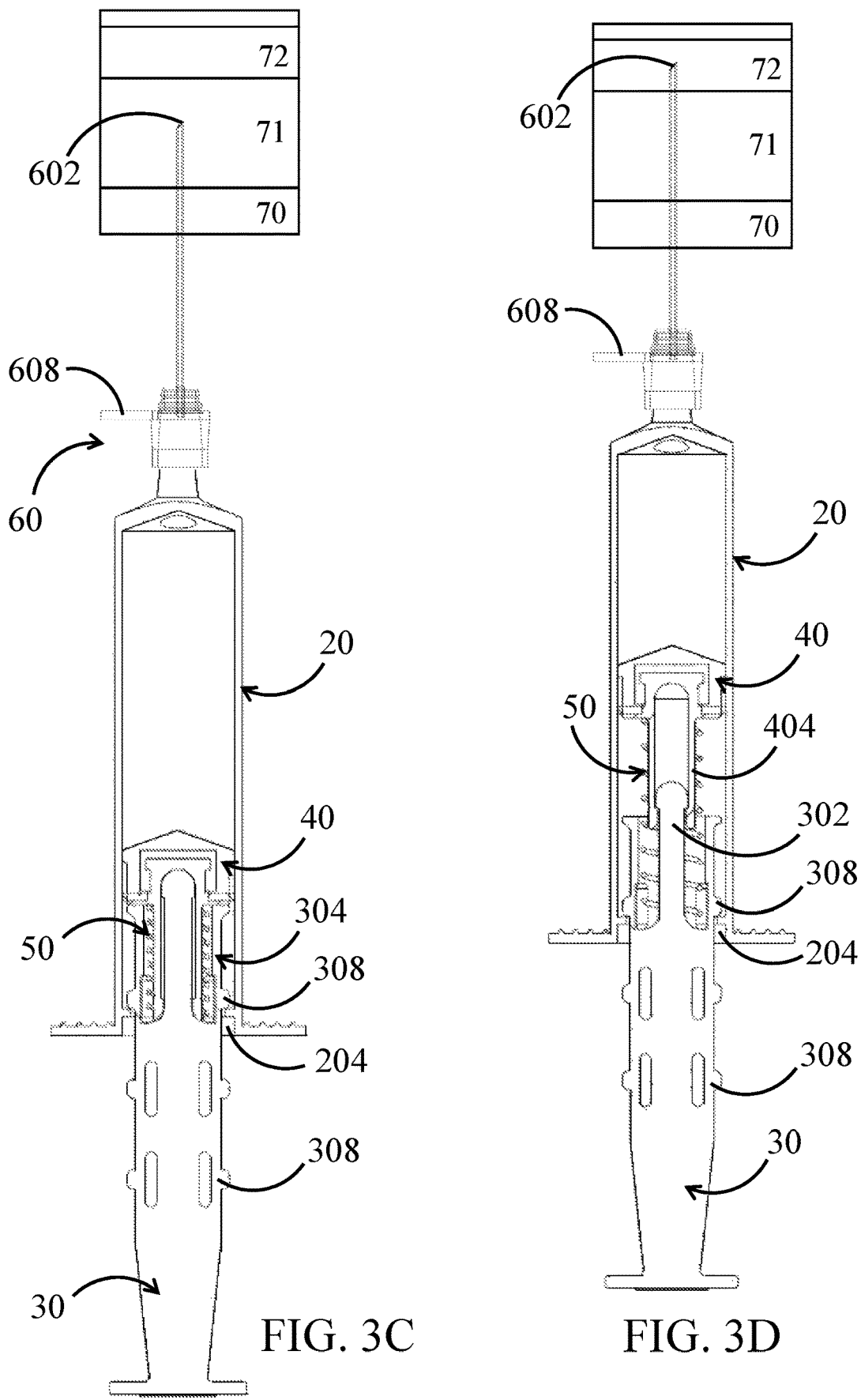
FIG. 3C is the syringe with the needle at a compressed length S2.
FIG. 3D is the syringe after sensing pressure changed.

As previously discussed, the device 10 (e.g., the syringe) includes the basic length S1 where the biasing element has the maximal length. The device 10 also includes a second length (i.e., a compressed length S2) when the length of the biasing element decreases. In another embodiment, the device 10 may also include a third length (i.e., a stretched or tensioned length S3) when the length of the biasing element increases. As FIGS. 3B and 3C show, the device 10 switches from the basic length S1 (FIG. 3B) to the compressed length S2 (FIG. 3C) as the plunger 30 moves towards to the needle 60. In other words, the distance between the piston and the plunger is decreased. Specifically, the difference between FIGS. 3B and 3C is that the plunger 30 moves into the barrel 20 until the latch 308 passes the flange 204, so the plunger 30 is fixed at a position (i.e., the first position) relative to the barrel 20 for operation. Because the constituent (e.g., the gas or the fluid/liquid) in the barrel 20 is incompressible or can only be compressed for a limited extent, the piston 40 is prevented from moving forward. In another aspect, the higher pressure at the needle tip prevents the piston from moving forward. In the embodiment disclosed in FIGS. 3B and 3C, the constituent is liquid. In other words, the piston 40 is at a first position relative to the barrel 20. In other words, the combined force from the liquid and the plunger 30 compresses the biasing element 50 (i.e., from the basic length S1 to a compressed length S2). Also, the cylindrical body 404 is fully received by the plunger 30 and covered by the sheath 304. The difference in length of the biasing element 50 between the basic length S1 and the compressed length S2 is the same as the distance that the latch 308 moves to mate with the flange 204 of the barrel 20. Accordingly, the syringe enables the operator to detect a desired cavity (e.g., the body cavity) during the compressed length S2 and the detection result is easily and readily identifiable.

FIG. 3D illustrates the configuration of the device 10 and the components thereof when the needle tip 602 reaches a specific location of as mass. During the advancement of the needle tip 602, the biasing element 50 continues to supply pressure/force against the liquid. When the needle tip 602 is at a solid body mass, as illustrated in FIG. 3C, there is no room for the liquid to escape. Therefore, the pressure within the barrel 20 is maintained. As the needle tip 602 advances and arrives a desired body cavity 72 (e.g., a particular epidural space), the needle tip 602 is no longer blocked. The constituent will be injected into the body cavity due to the force applied by the biasing element 50 as FIG. 3D shows. Correspondingly, the piston 40 moves forward, i.e., away from the operator and the plunger, as the biasing element 50's degree of compression reduces. In other words, the piston 40 moves from the first position to a second position relative to the barrel 20, and the distance between the piston and the plunger increased during the position change. The foregoing process stops until the pressure within the barrel 20 equals or balances the pressure at the body cavity 72. Alternatively, the process stops until the pressure is fully released (i.e., when the biasing element 50 is back to the basic length S1). In yet some other situations, the process stops when the piston 40 is fully extended from the plunger 30. In such case, the cylindrical body 404 is grabbed by the sliding part 302 and can no longer move forward. In sum, the piston 40 moves forward and away from the plunger 30 when the needle tip 602 reaches a predetermined body cavity. The movement of the piston 40 is easily identifiable by human eyes. In certain embodiments, the piston moves for about 2-4 centimeters when a pressure change is detected. In some other embodiments, the piston moves for at least about 1 centimeter when a pressure change is detected. A person having ordinary skill in the art would understand that the amount of movement of the piston is not so limited and any movement easily identifiable by a human operator is within the scope of this disclosure. Accordingly, the device 10 provides a clear visual signal of pressure change for the operator to confirm that the needle tip 602 reached a correct position. The visual signal may include a visible movement of the piston 40, presence of specific notice when the elongated bar is no longer covered by the sheave 304, or a change of colors that are distinct, and so on.

The following description will further describe the detail and the benefit of the device 10 of the present disclosure. When the syringe is under the compressed length S2 as FIG. 3C shows, the operator can just hold and push the handle 608 of the needle to advance the needle tip without directly operating (e.g., pushing) the plunger 30 or the barrel 20. In other words, the operator can focus on guiding the needle by controlling the handle 608 without moving other parts of the syringe. If the operator need to withdraw the needle or change the needle direction during the procedure, he/she can switch the syringe from the compressed length S2 to the basic length S1 of the biasing element 50 by withdrawing the plunger 30 to uncouple the latch 308 from the flange 204. Accordingly, the biasing element 50 applies no force to the liquid in the syringe, and the syringe returns to the status as FIG. 2 shows. After the direction of the needle is adjusted, the operator can easily switch the syringe to the sensing mode by advancing the plunger 30 to a position as FIG. 3C shows. Again, at such instance, the biasing element 50 is at the compressed length S2 and the syringe is at the sensing mode. Note that the syringe is only activated to the sensing mode when is required, thereby reducing the risk of erroneous reads. The device 10 of the present disclosure provides a simple and reversible mechanism to achieve the aforementioned goals. The mechanism of the present disclosure may prevent the fluid in the device 10 being injected into soft tissues (e.g., fascia, fibrous tissue, fat and synovial membrane) before the needle tip 602 reaches the proper location. For example, the operator can easily switch the device 10 to the non-sensing mode (no force from the biasing element 50 pushing the piston 40) when adjusting the route of the needle so the constituent in the barrel 20 won't accidentally enter undesired body parts.

As FIG. 4A shows, more than one latches are used to facilitate multiple attempts of sensing to reduce the risk of false positive. For example, under a false positive condition (i.e., the needle tip enters the soft tissue 73 rather than the real target cavity such as epidural and the piston 40 moves forward), the syringe can be re-switched to the sensing mode by pushing the plunger until the second set of latches and the flange 204 are coupled, as FIG. 4A shows. Thereafter, the operator can operate the device 10 based on the disclosure herein and identify a pressure change by reading the visual signal, as FIG. 4B shows.

In sum, the device 10 of the present disclosure provides an effective method to verify whether the location of the needle tip is at a desired location (e.g., a cavity) in the body mass. In the beginning of the procedure, the operator can advance the plunger to couple the latch and the flange so as to switch the syringe to the sensing mode as FIG. 3C shows. Further, the operator can proceed to advance the needle tip further into the mass, searching for the cavity. When the needle tip arrives at the body cavity 75, a visual signal will be presented, which is the result of the biasing element 50 returning to the basic length S1, as FIG. 3D or 4B shows. Subsequently, the syringe can be removed from the hub 606, which is ready for subsequent procedures.

Figure 5A:
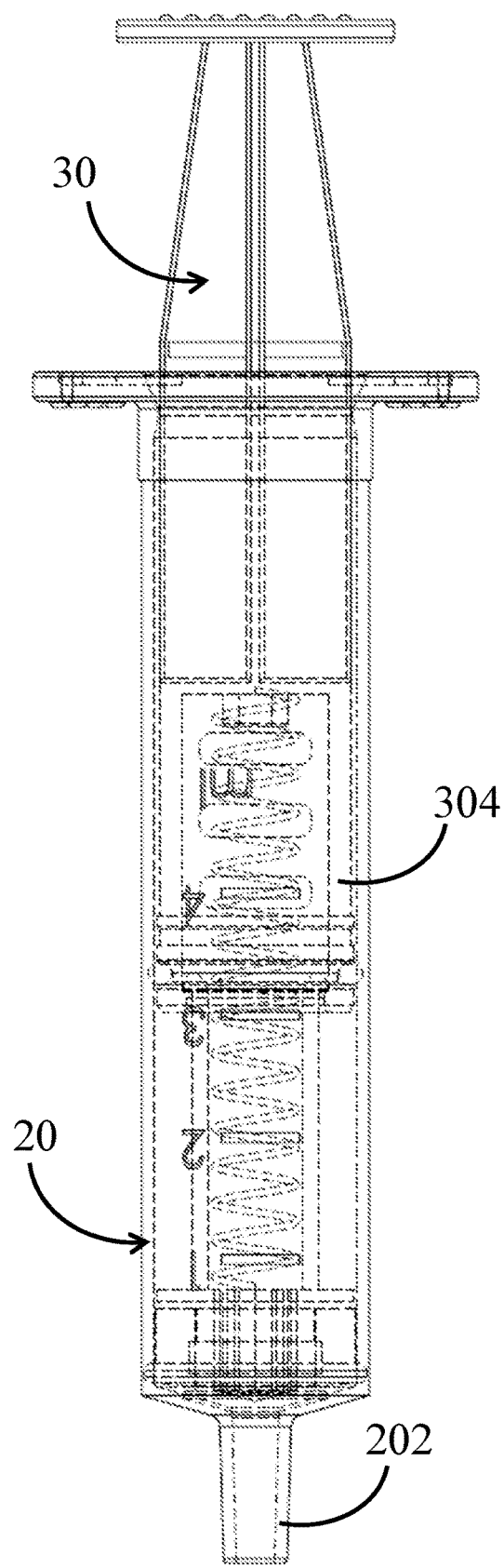
FIG. 5 series include a perspective view (FIG. 5A) and a sectional view (FIG. 5B) of a syringe in accordance with some embodiments of the present disclosure.
Figure 5B:
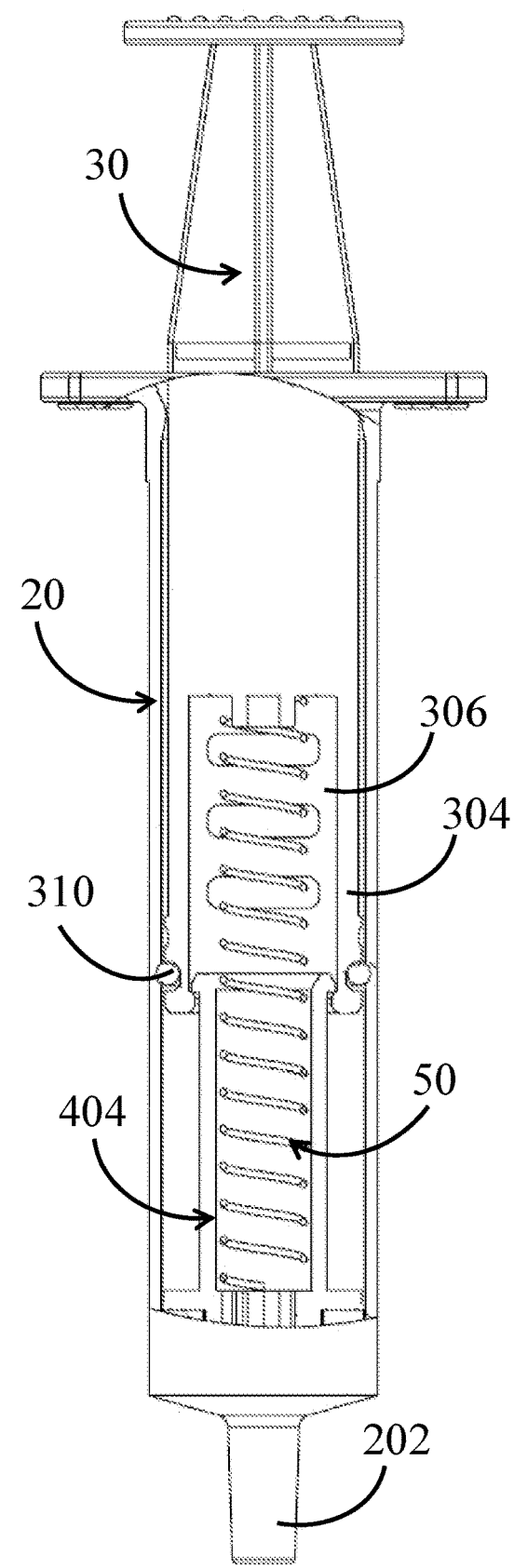

FIGS. 5A and 5B illustrate another exemplary embodiment wherein the device 10 is a syringe that includes the similar elements (e.g., a barrel 20, a plunger 30, piston 40, a biasing element 50, etc.) as FIGS. 1-4 show. The major difference between the syringes of FIGS. 5 and 1 is that there is no latch 308 but a stopper 310 in the syringe. In some exemplary embodiments, the stopper 310 is configured at one end of the plunger 30, as FIG. 5B shows. Furthermore, the stopper 310 is an elastic ring surrounding the outer surface of the plunger 30, and disposed between the sheath 304 of the plunger 30 and the inner wall of the barrel 20. Therefore, the stopper 310 can create resistance between the barrel 20 and the plunger 30, allowing the operator to maintain the plunger 30 at certain desired positions relative to the barrel 20. The stopper 310 may be specifically designed to fit between the barrel 20 and plunger 30. It is to be noted that although the syringe in FIG. 5 has a slight different design, the operation procedure is identical. That is, the syringe enables an operator to detect pressure change (signal of reaching a specific body part) by providing an easily identifiable visual signal.

Figure 6C:
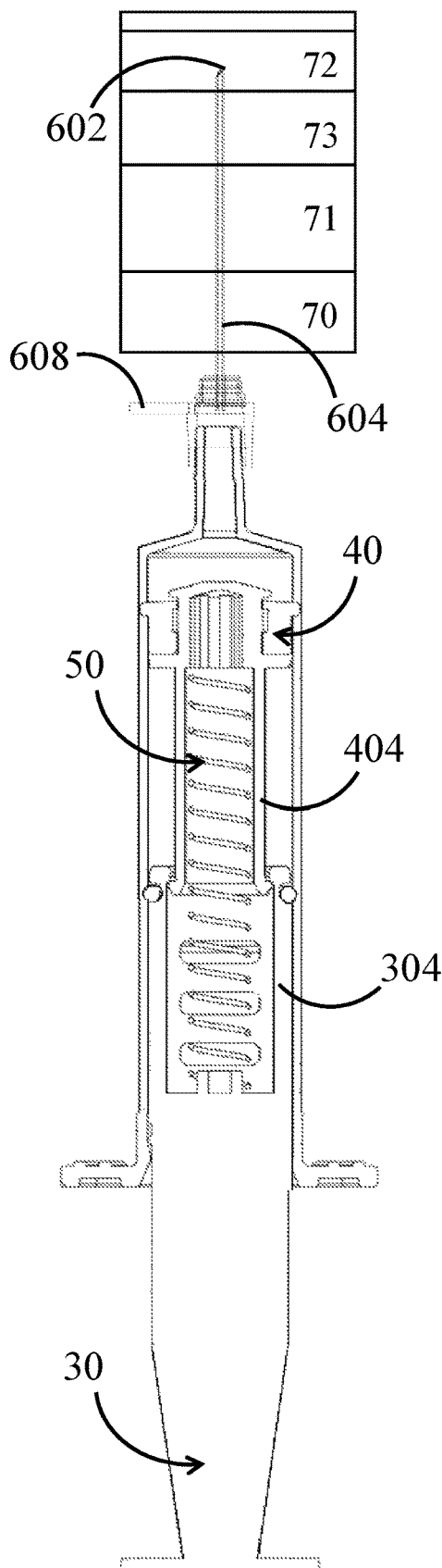
FIG. 6C is the syringe after sensing a pressure changed.

Attention is now directed to FIG. 6A. In some embodiments, the operator can let the tubular needle 604 pierces through the skin 70 to a specific depth by pushing the handle 608 in the first place. On the other hand, the operator can draw the constituent (e.g., fluid or air) into the barrel 20 by pulling the plunger 30. The needle and the syringe then are connected as FIG. 6A shows. At this instance, the syringe is under the basic length S1. Next, the operator switches the syringe from the basic length S1 to the compressed length S2 by advancing the plunger 30 to the first position by compressing the biasing element 50. In others words, the plunger 30 moves towards the piston 40. It is worth noting that, the compressed length of the biasing element 50 may be flexible and the further compressed state can still be activated. Specifically, because the stopper 310 on the plunger 30 provide a resistance force (e.g., friction) greater than the force provided by the biasing element 50, the stopper 310 secures the plunger 30 at a certain position as the operator pushes the stopper 310 to the certain position. In other words, the stopper maintains the force to the constituent by securing the plunger 30 without movement and keeping the biasing element compressed when the operator pushes the plunger 30 to the certain position. As FIG. 6B shows, the biasing element 50 is fully compressed (i.e., under the sensing mode) and the sheath 304 completely covers the cylindrical body 404 of the elongated bar. Because the friction between the stopper 310 and the inner surface of the barrel 20 is greater than the compression force of the biasing element 50, the position of the plunger 30 is secured. In the following procedures, the operator can use both hands to push the handle 608 and guide the needle tip 602 to penetrate the body mass. As FIG. 6C shows, when the needle tip 602 reaches the cavity 72, the piston 40 and the elongated bar move forward towards the distal end of the barrel 20, and the biasing element 50 returns to the basic length S1. The movement of the piston 40 provides a visual signal to the operator.

Figure 6D:
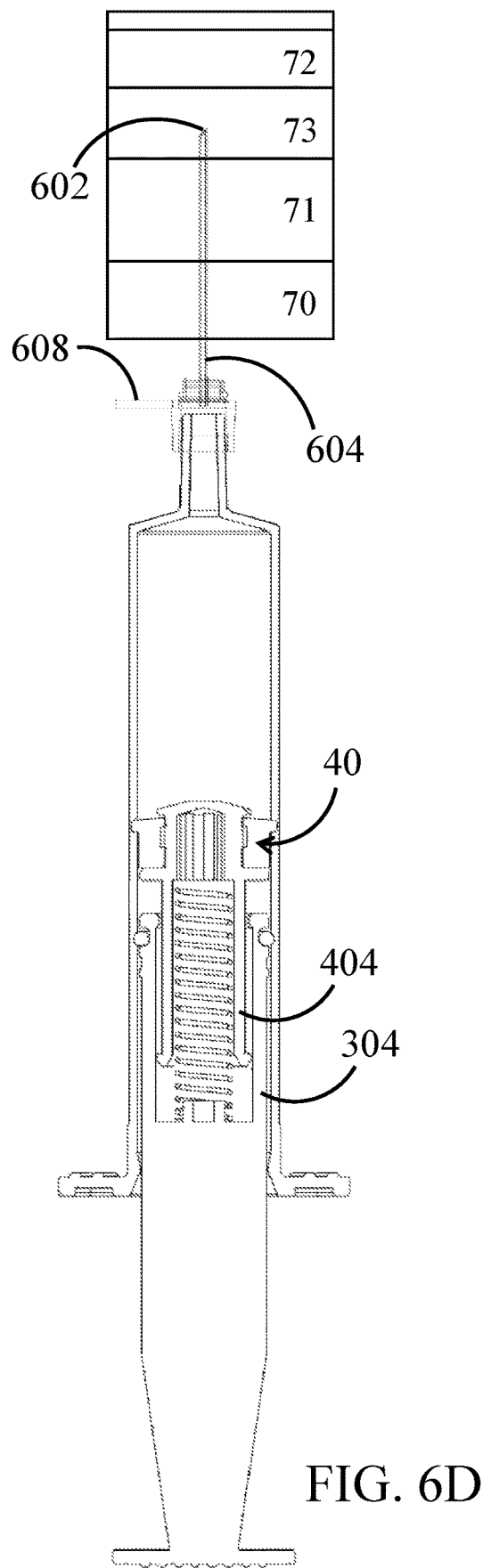
FIG. 6D is the syringe that demonstrates a false positive result.

If the syringe is under a false positive condition (as FIG. 6D shows), where the piston 40 only moves partially (i.e., the biasing element 50 is not fully released), the operator can again push the plunger 30 until the cylindrical body 404 is fully covered by the sheath 304 and re-guide the needle tip 602 further into the body mass to search for the proper location. In other words, an operator can easily switch the device 10 back to the sensing mode without withdrawing the needle from the mass.

In other embodiments, the syringe further includes markers (not shown) on the cylindrical body 404 of the piston 40. Therefore, an indicator (e.g., an indicator window) (not shown) on the sheath 304 of the plunger 30 can highlight the movement of the piston through a scale or a color mark on the surface of the sheath 304.

Figure 7:
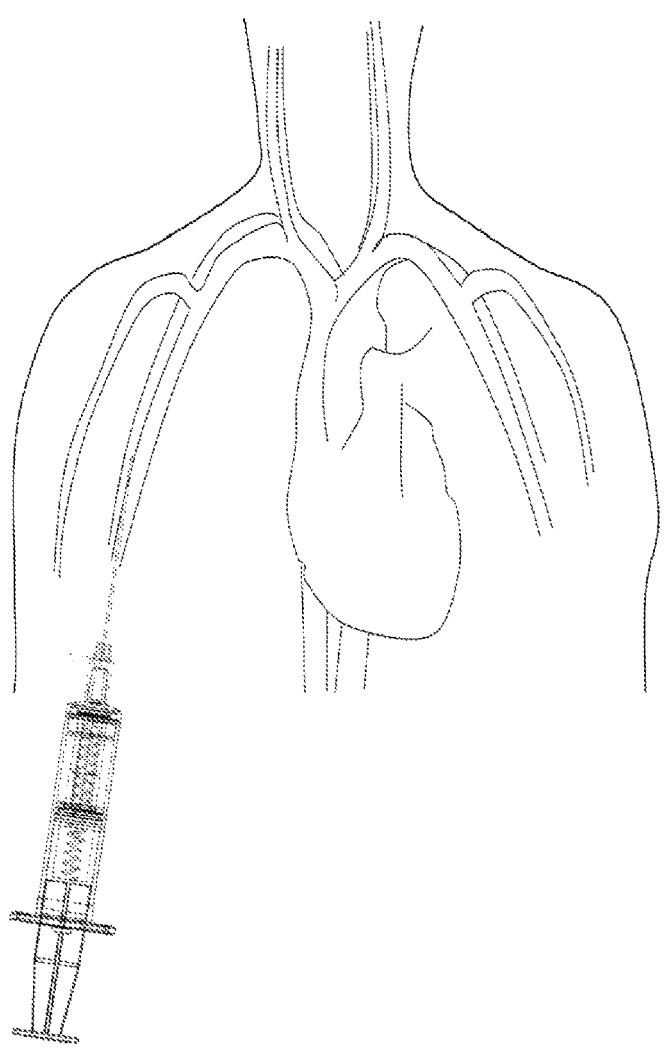
FIG. 7 is an illustration of an exemplary syringe operation in accordance with some embodiments of the present disclosure.

The central venous catheterization is another application of the present disclosure. FIG. 7 is a schematic view of a human body. To insert the catheter, the first thing is to insert a needle into a vein without puncturing the artery. Physicians can use conventional methods, such as the seldinger technique, to insert a central venous catheterization (hereinafter the "CVC") into a vein with the help of a pre-inserted needle. Accordingly, the needle can be precisely place into the vein by the CVC procedure.

Figure 8:
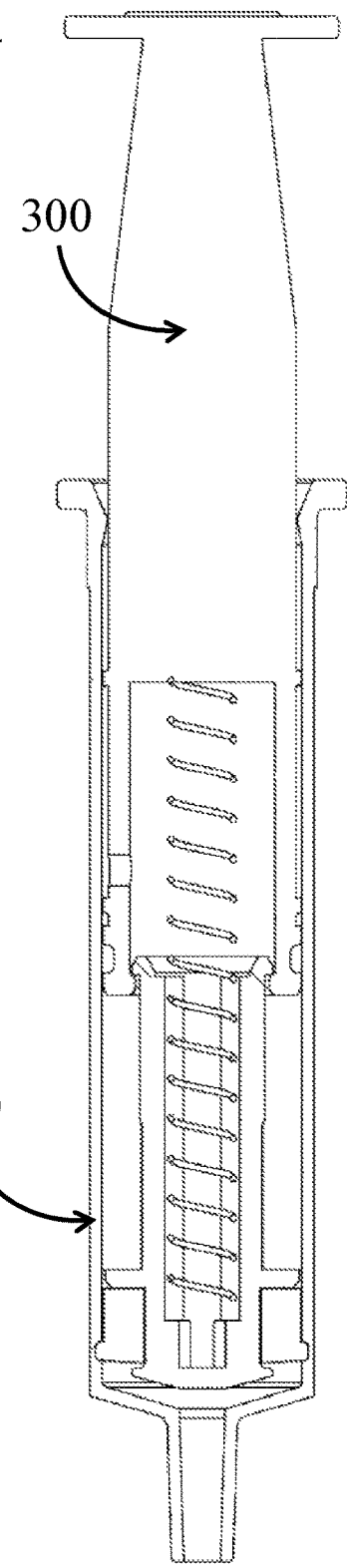
FIG. 8 is a sectional view of the syringe for CVC application in accordance with some embodiments of the present disclosure.

The present disclosure further provides a device 100 (e.g., a syringe) having similar elements as the syringes in the previously disclosed embodiments, and the device 100 is designed for use in the CVC procedure. FIG. 8 is a sectional view of the syringe for CVC application. The syringe for CVC application does not include any latch or stopper at the plunger 300. In other words, there is no resistance force or friction between the plunger 300 and the barrel 200 and the plunger 300 is capable sliding freely within the barrel 200. Furthermore, the operation procedure of the CVC syringe is also different from the syringe in the previous descriptions, although both of them can detect and signal pressure change.

Figure 9A:
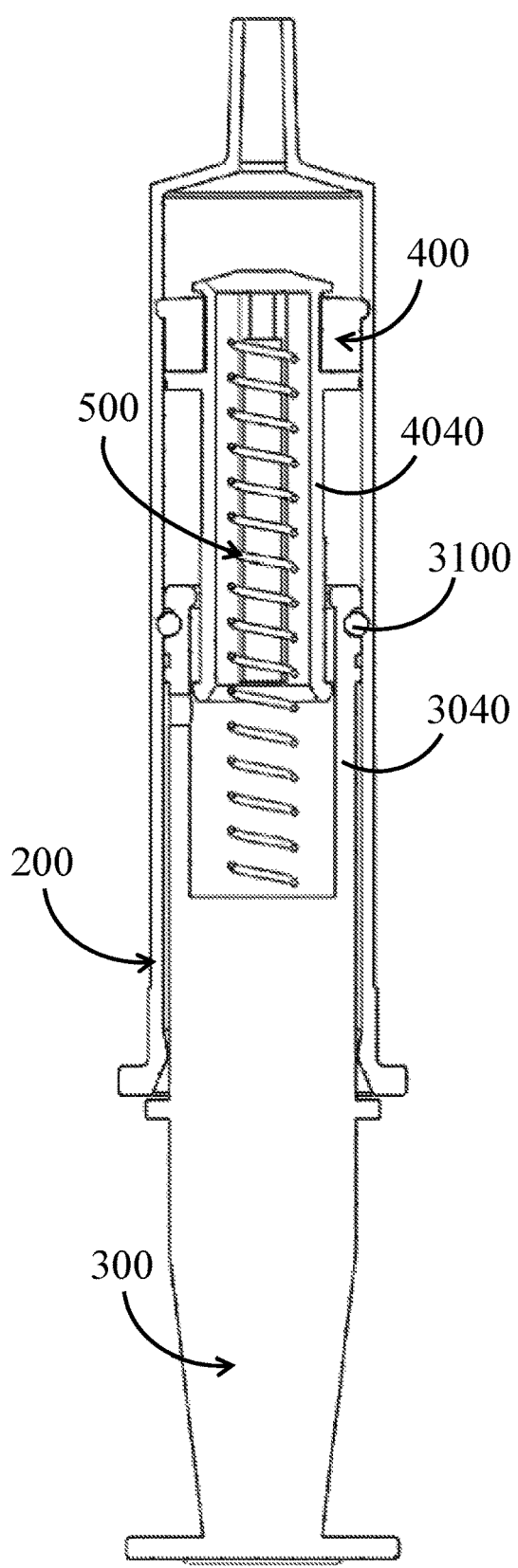
FIG. 9A is the syringe for CVC application that demonstrates where the needle tip thereof reaches a vein.
Figure 9B:
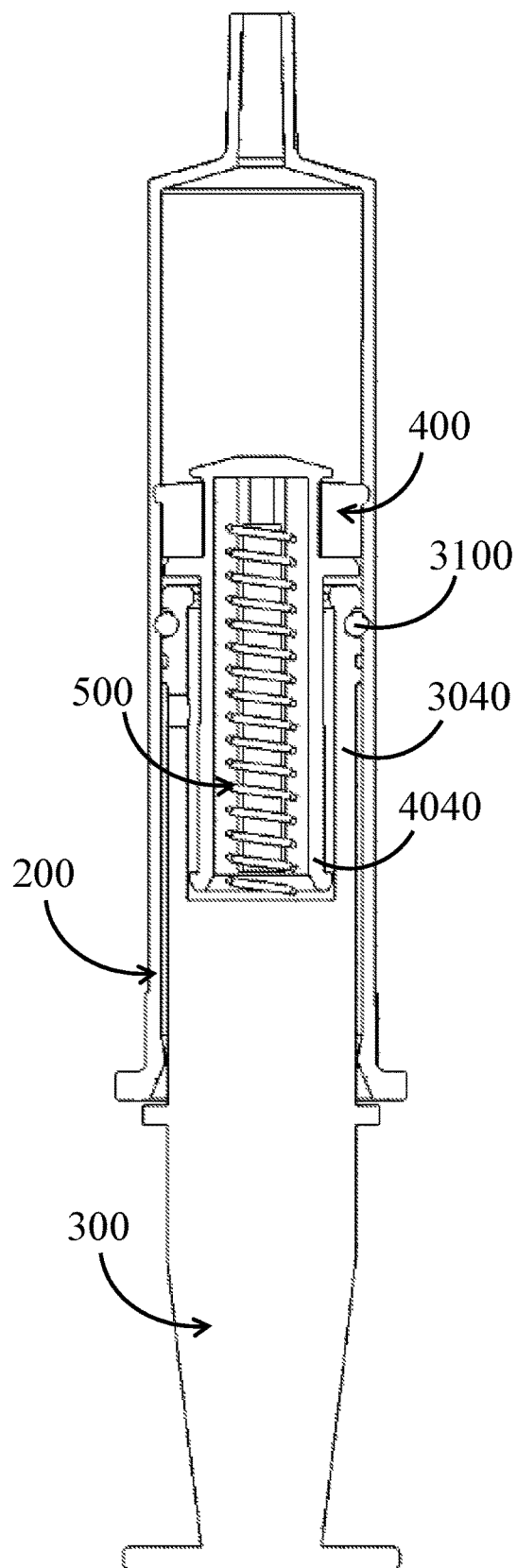
FIG. 9B is the syringe for CVC application where the needle tip thereof reaches an artery.

The following description will detail the syringe for the CVC application. As FIG. 9A shows, the syringe contains no constituent and the space inside the barrel 200 is under a negative pressure condition. Furthermore, the negative pressure condition is created by partially withdrawing the plunger 300 backward. Specifically, in the initial preparation procedure, the operator just need to connect the syringe and the needle, and slightly pull the plunger 300 to induce the blood reflux (i.e., to create a negative pressure inside the barrel 200). Then, the operator can further conduct subsequent procedures to guide the needle tip to a vein. When the blood reflux is observed by the operator, he/she can confirm whether the needle tip is inserted within a vein or an artery by checking the position of the piston 400. If the position of the piston 400 remains at the first position, which means the biasing element 500 (e.g., spring) is under the basic length S1, the operator knows that the needle tip is within the vein rather than the artery. The reason is that the pressure of the vein is lower than the force provided by the biasing element 500. On the contrary, the pressure of an artery is higher than the force provided by the biasing element 500, and this causes the piston 400 to move. Therefore, the biasing element 500 will be compressed, and the relative position of the piston 400 to the barrel 200 now moves to the second position (i.e., the relative distance between the piston 400 and the plunger 300 becomes shorter). It signals the operator that the needle tip is within the artery. The operator must withdraw the needle and then find the correct vein to avoid complications. Note that the mechanism (i.e., the movement of the piston) identifying whether the needle tip reached a vein is opposite to the previous embodiments where the needle is designed to reach a cavity. The reason is that the pressure inside the vein is lower compared to the force provided by the biasing element 500, as opposed to the artery where it has a higher pressure. Hence, the high pressure in the artery forces the piston 400 backwardly, i.e., away from the distal end of the barrel 200 until the biasing element 500 is fully compressed, as FIG. 9B shows. In other words, the piston 400 moves away from the distal end when the syringe identifies an increasing pressure when the needle tip reaches the artery. Therefore, the movement of the piston 400 identifying a blood vessel is different from the one identifying a cavity. Specifically, the piston 400 that detected a body cavity will move from the first position to the second position whereas one that detected a vein will remain station. Here, at the sensing mode of the syringe for the CVC application, the biasing element 500 is at the basic length S1, which has a maximum length.

In another embodiment, the present disclosure provides another syringe used in the CVC application with similar elements as FIGS. 8-9 show. The difference is that the plunger 300 is received by the piston 400. Specifically, the cylindrical body 4040 is not covered by the sheath 3040, but instead covers the sheath 3040 of the plunger 300. In another word, the cylindrical body 4040 of the piston 400 surrounds or encloses the sheath 3040 of the plunger 300. Moreover, the stopper 3100 is configured at approximately the mid-section of the plunger 300 connected to the proximal end sheath 3040. The spring 500 connects to the plunger 300 and the piston 400 respectively. Further, the spring 500 is received by the plunger 300 and the piston 400. This design provides accurate movement of the piston 400 and identifiable visual signal for pressure change.

The piston 400 moves towards the plunger when the needle tip reaches the artery, and the operator can redirect the needle. If the piston does not move or only partially moves, it means that the needle tip is within the vein (i.e., the desire result).

In one aspect, the pressure in the artery is about 14 kPa and the pressure in the vein is about 1.2 kPa for a normal human. The corresponding pressure that the biasing element 500 of the device 100 used in the CVC application shall be in the range between about 1.2-14 kPa and more preferably about 2 kPa. In another aspect, the pressure in most of the epidural of the patients is ≤0 kPa. Therefore, the device 100 can be used in epidural application as long as the biasing element 500 can provide a greater pressure to the constituent that compared to the pressure in the epidural applied to the constituent. Nevertheless, in order to prevent the needle from being blocked by the tissue during the piercing process, the compression load of the biasing element may need to be increased. In some embodiments, when the plunger is pulled out to the limit without separating from the syringe (i.e., the syringe is at the maximal length), the biasing element (e.g., a spring) is still partially compressed, and the compression load of the spring is about 90 g. In other words, a force greater than 90 g is required to compress the biasing element when the syringe in the basic length S1. However, the foregoing are not meant to be limiting and the compression force of the spring may be so adjusted as long as the resulting syringe can display identifiable visual signal when there's pressure change. Furthermore, the compression load of the biasing element may correspond to the piston's range of movement during pressure change. In other words, the more force is applied to the piston, the movement of the piston will be more clear when the needle tip reaches the desired location (e.g., the cavity). However, note that too much force applied by the biasing element may induce gas leakage (i.e., resulting in false positive), and the latches or the stopper at the plunger need to provide more resistance or friction to prevent unwanted plunger movement. Therefore, the preferable compression load of the biasing element 500 is about 200 g, which creates about 16 kPa of pressure to the constituent inside the barrel 200 when the tubular part of the elongated bar is fully submerged into the sheath of the plunger. This serves to ensure that the movement of the piston 400 relative to the plunger 300 is significant such that an operator can detect the visual signal more easily.

LISTING OF ELEMENTS

- 10, 100 Device
- 202 Connecting tube
- 204 Flange
- 20, 200 Barrel
- 30, 300 Plunger
- 302 Sliding part
- 304, 3040 Sheath
- 308 Latches
- 310, 3100 Stopper
- 40, 400 Piston
- 404, 4040 Cylindrical body
- 406 Throat
- 50, 500 Biasing element
- S1 Basic length
- S2 Compressed length
- 60 Needle
- 602 Needle tip
- 604 Tubular needle
- 606 Hub
- 608 Handle
- 70 Skin
- 71 Subcutaneous tissue
- 72 Cavity
- 73 Soft tissue
- A-A' Cross-section line

What is claimed is:

1. A syringe for detecting pressure change, comprising:
   a barrel defining a reservoir for receiving a constituent, and the barrel includes a proximal end and a distal end with an outlet;
   a piston movable within the reservoir;
   a plunger movable within the reservoir and slideably engaged with the piston;
   a biasing element disposed between the plunger and the piston, wherein the biasing element's change in length corresponds to a relative distance between the plunger and the piston; and
   a needle, detachably connected to the distal end of the barrel, wherein whether the needle is moved to a desired location from an undesired location of a mass is indicated by the piston's change of position corresponding to a pressure difference between the desired location and the undesired location, and the piston is at a first position relative to the plunger when the biasing element is at a first length, and the piston moves from the first position to a second position in response to the biasing element's change of the first length resulting from a pressure change inside the reservoir when the needle reaches the desired location of the mass,
   wherein the piston's change of position is visually detectable.

2. The syringe according to claim 1, wherein the plunger comprises a stopper for creating a resistance between the barrel so as to secure the plunger at a third position.

3. The syringe according to claim 1, wherein the stopper is a ring made of elastomer.

4. The syringe according to claim 1, wherein the constituent in liquid or gas form.

5. The syringe according to claim 1, wherein the biasing element includes a spring.

6. The syringe according to claim 1, wherein the biasing element is received by the plunger.

7. The syringe according to claim 1, wherein the needle includes a needle tip.

8. The syringe according to claim 1, wherein the piston moves from the first position to the second position relative to the plunger when the pressure inside the reservoir is decreasing.

9. The syringe according to claim 1, wherein a material of the biasing element includes: metal, plastic, rubber or a combination thereof.

10. The syringe according to claim 1, wherein a pressure at the desired location of the mass is different from that at the undesired location of the mass.

11. The syringe according to claim 1, wherein the desired location of the mass is a cavity.

12. The syringe according to claim 1, wherein a direction of the piston from the first position to the second position is moving closer to the plunger.

13. The syringe according to claim 1, wherein a direction of the piston from the first position to the second position is moving away from the plunger.

14. The syringe according to claim 1, wherein a degree of compression of the biasing element is less when the piston is in the second position than in the first position.

15. The syringe according to claim 1, wherein the piston is at the first position when the needle enters the undesired location of the mass but before reaching the desired location.

16. The syringe according to claim 1, wherein the piston immediately moves to the second position upon the needle reaching the desired position.

17. The syringe according to claim 1, wherein the piston moves at least 1 centimeter from the first position to the second position.

18. The syringe according to claim 1, wherein the piston's change of position is represented by a signal at the piston or the plunger.

19. The syringe according to claim 18, wherein the signal is a color or a change of color.

20. A syringe for detecting pressure change in a mass, comprising:
- a barrel defining a reservoir for receiving a constituent, and the barrel includes a proximal end and a distal end with an outlet;
- a piston movable within the reservoir;
- a plunger movable within the reservoir and slideably engaged with the piston;
- a biasing element disposed between the plunger and the piston, wherein the biasing element's change in length corresponds to a relative distance between the plunger and the piston; and
- a needle, detachably connected to the distal end of the barrel,
- wherein the piston is at a first position relative to the plunger when the biasing element is at a first length, and the needle's reaching a desired location of a mass from a first location creates a first pressure change in the reservoir and the first pressure change does not cause a visually detectable change in the first length of the biasing element such that the piston remains at the first position,
- wherein the needle's reaching an undesired location of the mass from the desired position creates a second pressure change in the reservoir and the second pressure change causes a visually detectable change in the first length of the biasing element, such that the piston moves from the first position to a second position.

21. The syringe according to claim 20, wherein the second pressure change is an increase in pressure.

22. The syringe according to claim 20, wherein a direction of the piston from the first position to the second position is moving closer to the plunger.

23. A syringe for being positioned through detecting pressure change, comprising:
- a barrel defining a reservoir for receiving a constituent, and the barrel includes a proximal end and a distal end with an outlet;
- a piston movable within the reservoir;
- a plunger movable within the reservoir and slideably engaged with the piston;
- a biasing element disposed between the plunger and the piston, wherein the biasing element's change in length corresponds to a relative distance between the plunger and the piston; and
- a needle, detachably connected to the distal end of the barrel,
- wherein the piston is at a first position relative to the plunger when the biasing element is at a first length, and the needle's reaching a desired location of a mass from a first location creates a first pressure change inside the reservoir and the first pressure change causes a visually detectable change in the first length of the biasing element such that the piston moves from a first position to a second position,
- wherein the needle's reaching an undesired location of the mass from the desired location creates a second pressure change in the reservoir and the second pressure change does not cause a visually detectable change in the first length of the biasing element such that the piston remains at the second position,
- wherein the plunger comprises a stopper for creating a resistance between the barrel so as to secure the plunger at a third position.

* * * * *